US009585561B2

(12) United States Patent
Artsyukhovich

(10) Patent No.: US 9,585,561 B2
(45) Date of Patent: Mar. 7, 2017

(54) OPHTHALMIC SURGICAL MICROSCOPE WITH ADAPTIVE OPTICS FOR OPTICAL WAVEFRONT COMPENSATION

(71) Applicant: NOVARTIS AG, Basel (CH)

(72) Inventor: Alexander N. Artsyukhovich, Irvine, CA (US)

(73) Assignee: Novartis AG, Basel (CH)

( * ) Notice: Subject to any disclaimer, the term of this patent is extended or adjusted under 35 U.S.C. 154(b) by 152 days.

(21) Appl. No.: 14/341,743

(22) Filed: Jul. 25, 2014

(65) Prior Publication Data

US 2016/0022139 A1     Jan. 28, 2016

(51) Int. Cl.
| G02C 7/02 | (2006.01) |
| A61B 3/00 | (2006.01) |
| A61B 3/18 | (2006.01) |
| A61B 5/11 | (2006.01) |
| A61B 3/14 | (2006.01) |
| G02C 13/00 | (2006.01) |
| A61B 3/113 | (2006.01) |
| A61B 5/107 | (2006.01) |
| A61B 3/11 | (2006.01) |
| A61B 3/13 | (2006.01) |
| G02B 26/08 | (2006.01) |
| G02B 27/00 | (2006.01) |
| A61F 9/007 | (2006.01) |
| G02B 21/00 | (2006.01) |
| A61B 3/10 | (2006.01) |
| A61B 3/12 | (2006.01) |
| A61F 9/008 | (2006.01) |

(52) U.S. Cl.
CPC .............. A61B 3/13 (2013.01); A61B 3/0025 (2013.01); A61F 9/007 (2013.01); G02B 21/0012 (2013.01); G02B 26/0825 (2013.01); G02B 27/0068 (2013.01); A61B 3/1015 (2013.01); A61B 3/12 (2013.01); A61F 2009/00848 (2013.01)

(58) Field of Classification Search
CPC ....... A61B 3/13; A61B 3/1015; A61B 3/0025; G02B 27/0068; G02B 26/0825
See application file for complete search history.

(56) References Cited

U.S. PATENT DOCUMENTS

| 7,742,213 B2 | 6/2010 | Potsaid et al. |
| 2003/0007125 A1 | 1/2003 | Levine |

(Continued)

*Primary Examiner* — Thomas K Pham
*Assistant Examiner* — Cara Rakowski

(57) ABSTRACT

An ophthalmic surgical microscope can include a first light source configured to project a first light beam at an observer's eye. The microscope can include a first wavefront sensor. The first wavefront sensor can be configured to determine aberrations in the first reflection wavefront of a reflection of the first light beam. The microscope can include adaptive optical element(s). The adaptive optical element(s) can be controlled to modify the phase of incident light. The microscope can include a computing device in communication with the first wavefront sensor and the adaptive optical element(s). The computing device can be configured to generate the control signal to compensate for the aberrations and to provide the control signal to the adaptive optical element(s). A second light source and second wavefront sensor can be provided to compensate for aberrations of a subject's eye.

18 Claims, 3 Drawing Sheets

(56) References Cited

U.S. PATENT DOCUMENTS

| | | | |
|---|---|---|---|
| 2005/0018134 A1* | 1/2005 | Noda | A61B 3/132 |
| | | | 351/205 |
| 2006/0087617 A1 | 4/2006 | Roorda | |
| 2007/0171366 A1* | 7/2007 | Su | G01J 9/00 |
| | | | 351/205 |
| 2007/0273830 A1 | 11/2007 | Levine | |
| 2011/0267579 A1 | 11/2011 | Van Heugten et al. | |
| 2013/0169932 A1 | 7/2013 | Saito | |
| 2013/0182253 A1 | 7/2013 | Cui | |
| 2013/0190736 A1 | 7/2013 | Fabrikant et al. | |

* cited by examiner

OPHTHALMIC SURGICAL MICROSCOPE WITH ADAPTIVE OPTICS FOR OPTICAL WAVEFRONT COMPENSATION

BACKGROUND

Technical Field

Embodiments disclosed herein are related to ophthalmic surgical microscopes. More specifically, embodiments described herein relate to an ophthalmic surgical microscope including adaptive optical element(s) and wavefront sensor(s) to dynamically compensate for optical aberrations.

Related Art

Doctors can use surgical microscopes during ophthalmic surgical procedures to see fine details of a patient's eye. A successful procedure can depend on the doctor's ability to view the patient's eye clearly using the microscope. This can be challenging, however, because of artifacts of the doctor's eye and/or the patient's eye. For example, the doctor and/or the patient can have static vision problems. These can include refractive errors, astigmatism, other low order aberrations, and/or high order aberrations. Further, dynamic errors can arise during a surgical procedure. These include the presence of tear film in the doctor's eye, saline solution in the patient's eye, among others. The artifacts of the doctor's eye and/or the patient's eye interfere with the doctor's vision of the surgical field and can hinder the efficacy of a surgical procedure.

Some conventional methods can partially compensate for a doctor's and/or a patient's vision problems when using current surgical microscope models. The doctor can have refractive surgery to correct some vision problems, such as long term refractive errors. The doctor can wear spectacles to compensate for refractive errors and astigmatism. Wearing spectacles during the surgical procedure, however, can be uncomfortable for a doctor. Turning oculars of the microscope can be used to compensate for spherical refractive errors of the doctor and the patient. However, no microscope currently compensates for high order aberrations of the doctor's eye. And no microscope currently compensates for astigmatism and high order aberrations of the patient's eye. Further, no microscope compensates for dynamic errors that arise during the surgical procedure.

SUMMARY

The presented solution fills an unmet medical need with a unique solution to provide the combination of adaptive optical element(s) and wavefront sensor(s) in an ophthalmic surgical microscope to actively remove optical aberrations caused by vision problems of a doctor and/or a patient, as well as dynamic errors arising during a surgical procedure. As a result, the doctor's vision of the patient's eyes and the doctor's ability resolve fine details during a surgical procedure can be drastically improved.

Consistent with some embodiments, an ophthalmic surgical microscope disposed in an optical path between an observer and a subject includes: a first light source configured to project a first light beam at an eye of the observer, a reflection of the first light beam from the eye of the observer including a first reflection wavefront; a first wavefront sensor disposed in an optical path of a reflection of the first light beam from the eye of the observer, the first wavefront sensor being configured to determine aberrations in a first reflection wavefront of the reflection of the first light beam; an adaptive optical element disposed in the optical path between the observer and the subject, the adaptive optical element being configured to modify the phase of incident light to compensate for the aberrations in the first reflection wavefront in response to a control signal; and a computing device in communication with the first wavefront sensor and the adaptive optical element, the computing device being configured to generate the control signal to compensate for the aberrations in the first reflection wavefront and to provide the control signal to the adaptive optical element.

Consistent with some embodiments, a method of compensating for optical aberrations in an ophthalmic surgical microscope disposed in an optical path between an observer and a subject includes: projecting a first light beam at an eye of an observer; determining aberrations in a first reflection wavefront of a reflection of the first light beam from the eye of the observer; projecting a second light beam at an eye of the subject; determining aberrations in a second reflection wavefront of a reflection of the second light beam from the eye of the subject; and controlling an adaptive optical element disposed in the optical path between the observer and the subject to modify a phase of light in the optical path to compensate for the aberrations in the first and second reflection wavefronts.

Additional aspects, features, and advantages of the present disclosure will become apparent from the following detailed description.

Figure 1:
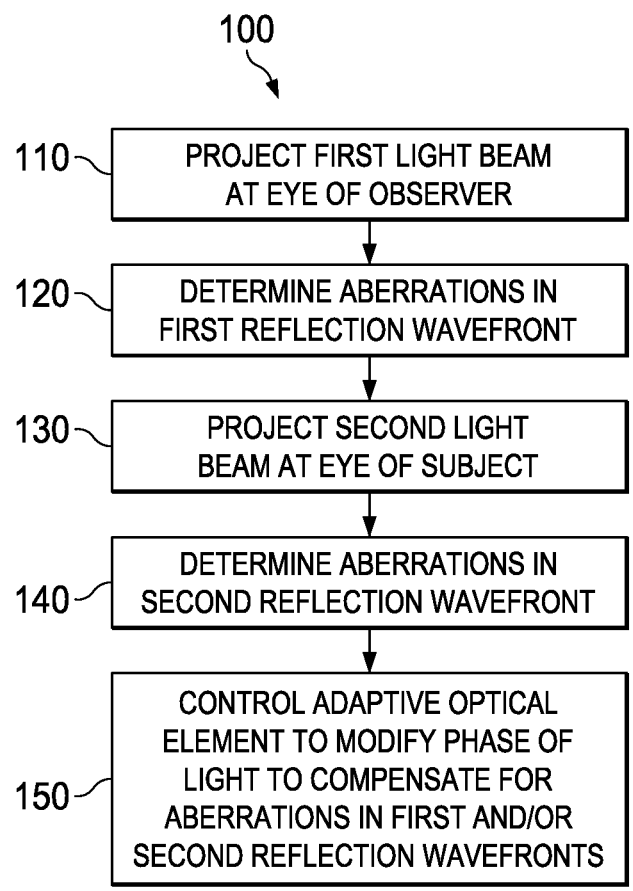
FIG. 1 is a flow diagram illustrating a method of compensating for optical aberrations in an ophthalmic surgical microscope disposed in an optical path between an observer and a subject.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

The present disclosure describes an ophthalmic surgical microscope with adaptive optical element(s) and wavefront sensor(s). The adaptive optical element and the wavefront sensor can be implemented in optical paths associated with the doctor and/or the patient. For example, a laser can be projected on the doctor's retina. A wavefront of light reflected from the retina can be detected by the wavefront sensor. The wavefront sensor can determine if the wavefront is curved (e.g., it includes phase aberrations) or flat (e.g., it does not include phase aberrations). The reflective or transmissive adaptive optical element can be controlled to modify the phase of light in the optical path between the doctor and the patient to compensate for any detected aberrations. A similar configuration can be implemented to correct optical aberrations associated with the patient.

The devices, systems, and methods of the present disclosure provide numerous advantages, including: (1) improving efficacy of surgical procedures by compensating for wavefront deformations resulting from a doctor's vision problems, including astigmatism and high order aberrations; (2) improving efficacy of surgical procedures by compensating for wavefront deformations resulting from a patient's vision problems, including astigmatism and high order aberrations; (3) increasing flexibility for surgical microscopes by providing dynamic wavefront compensation for optical aberrations arising during surgical procedures; and (4) increasing usability for surgical microscopes by maximizing surgical field sight for all doctors, regardless of varying degrees of problematic vision.

Figure 2:
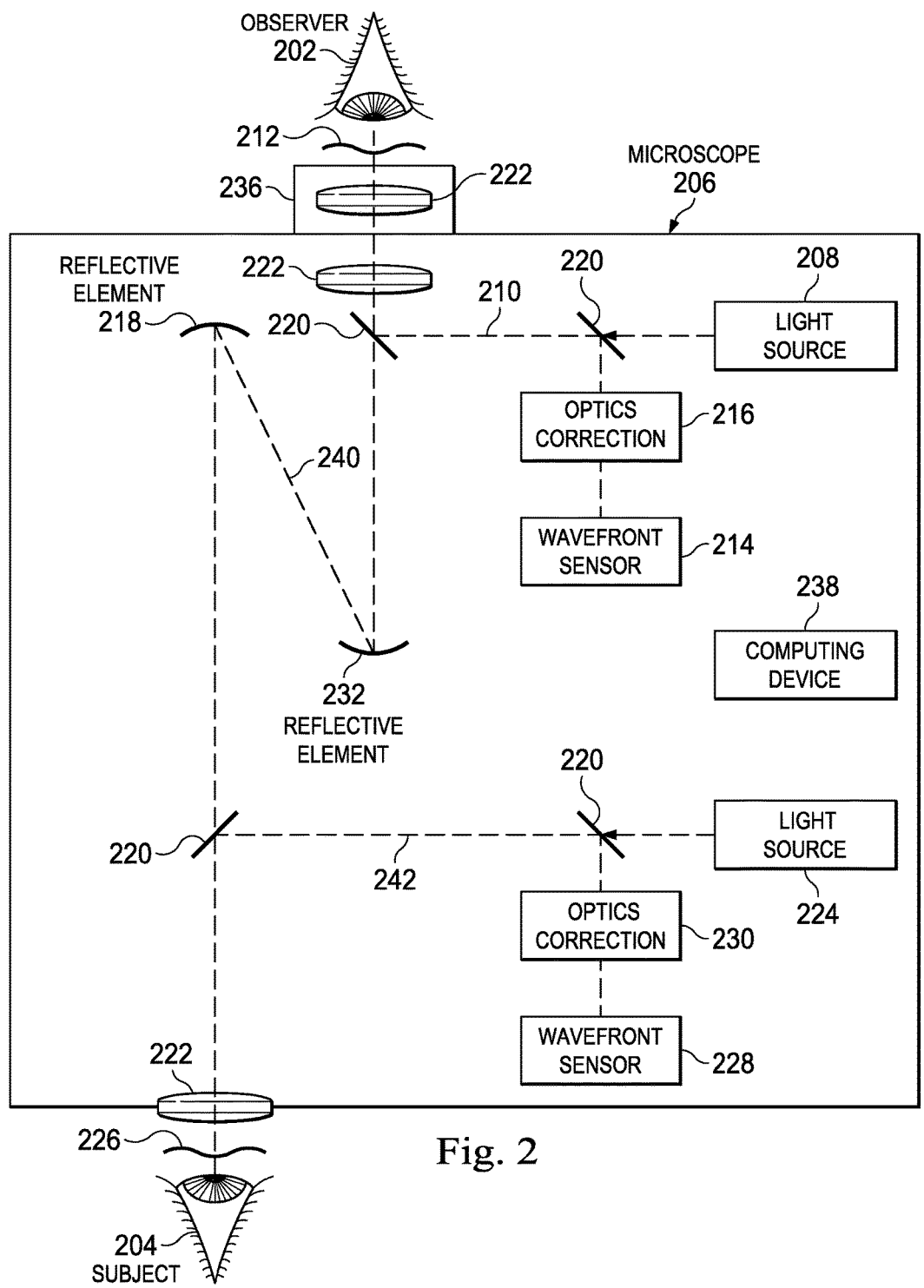
FIG. 2 is a diagram illustrating an ophthalmic surgical microscope.

FIG. 1 provides a flow diagram of a method 100 of compensating for optical aberrations in an ophthalmic surgical microscope disposed in an optical path between an observer and a subject. The method 100 can be further understood with reference to FIGS. 2 and 3, which illustrate ophthalmic surgical microscopes according to embodiments of the present disclosure. FIG. 2 illustrates a microscope 206 including reflective adaptive optical elements (e.g., reflective elements 218 and 232), and FIG. 3 illustrates the microscope 206 including a transmissive adaptive optical element (e.g., transmissive element 234).

Referring to FIG. 1, the method 100 can include, at step 110, projecting a first light beam at the eye of an observer. The method 100 further includes, at step 120, determining aberrations in a first reflection wavefront associated with the first light beam. Steps 110 and 120 can be associated with identifying optical aberrations of the observer.

Figure 3:
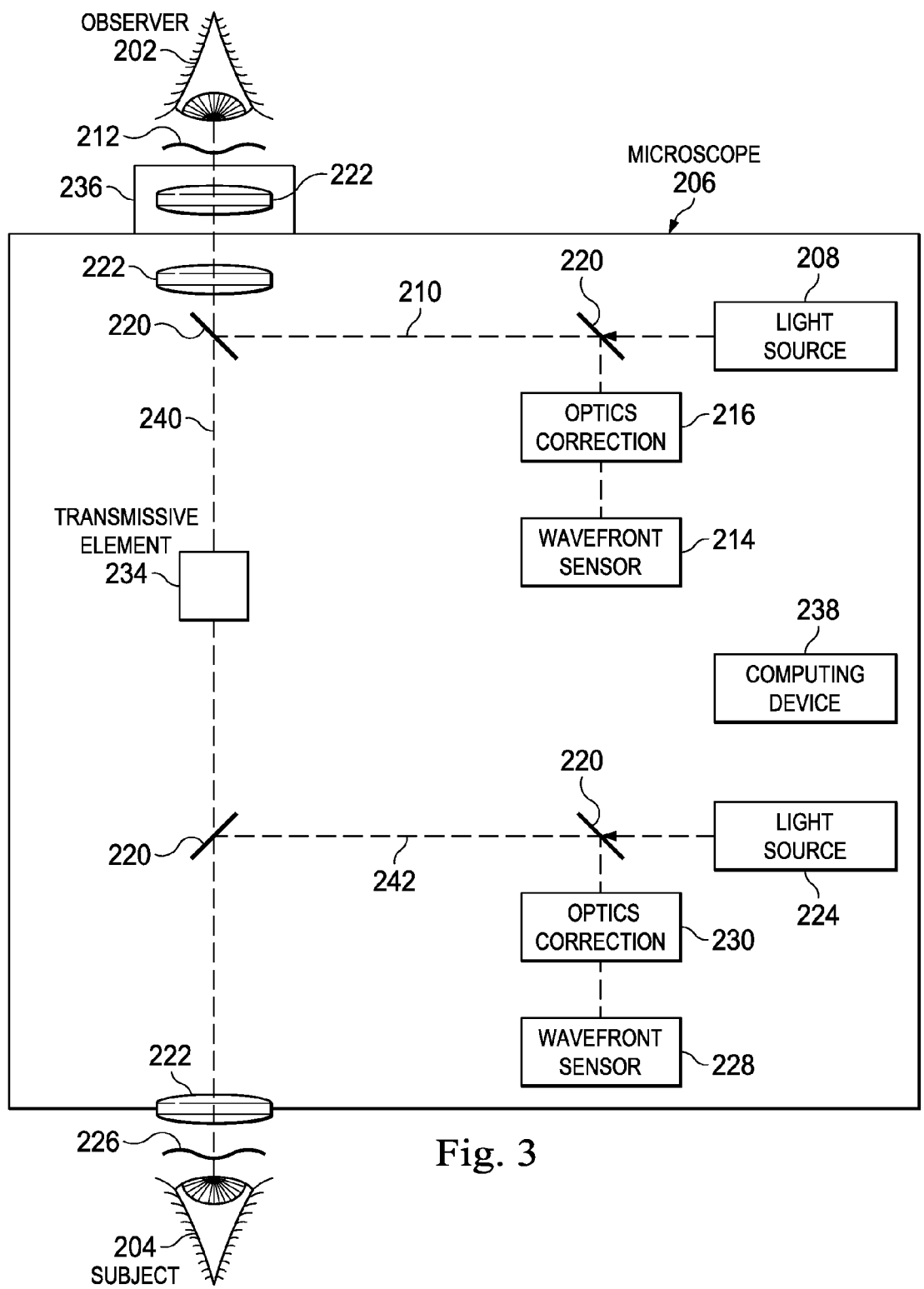
FIG. 3 is a diagram illustrating an ophthalmic surgical microscope.

As shown in FIGS. 2 and 3, an observer 202 can use an ophthalmic surgical microscope 206 to view the eye of a subject 204. The observer 202 can be a healthcare professional, such as a doctor or surgeon performing a diagnostic, surgical, and/or other medical procedure. The subject 204 can be a patient undergoing the medical procedure.

The microscope 206 can include a light source 208. The light source 208 can be, for example, a laser light source, super-luminescent diode(s), or other suitable light source(s). At step 110 (FIG. 1), the light source 208 can project a first light beam along an optical path 210 at the eye of the observer 202. The light source 208 can be configured to continuously or intermittently project the first light beam at the eye of the observer 202. The light source 208 can be in communication with the computing device 238. The computing device 238 can be configured to generate a control signal for and provide the control signal to the light source 208. The control signal can be based on a first wavefront compensation frequency that describes a frequency at which the microscope 206 compensates for optical aberrations associated with the observer 202. The control signal can be an electrical signal. The first wavefront compensation frequency can be adjustable (e.g., before and/or during the surgical procedure) based on the clinical objectives for wavefront compensation. For example, the first light beam can be projected at the eye of the observer 202 relatively infrequently, such as once a day, once during a surgical procedure, once every ten minutes, or other periods greater than, less than, and/or between those listed, to compensate for static vision problems. Projecting the light at a lower frequency can be associated with a lesser risk to the health of the observer 202 caused continuous or higher frequency irradiation of the retina. For example, the first light beam can be projected at a relatively higher frequency, such as once every thirty seconds, once a minute, or other periods greater than, less than, and/or between those listed, to compensate both for static vision problems and for dynamic errors arising during the surgical procedure (e.g., tear film in the eye of the observer 202). Projecting the light at a higher frequency can be associated with maximizing vision of the surgical field for the observer 202 during the surgical procedure.

A reflection of the first light beam off of the eye of the observer 202 includes a reflection wavefront 212. The reflection wavefront 212 can be received at a wavefront sensor 214. The wavefront sensor 214 can be disposed in the optical path 210 of the reflection wavefront 212. One or more optical paths (e.g., optical paths 210, 240, and 242) can include beam splitters 220. At step 120 (FIG. 1), the wavefront sensor 214 can determine phase aberrations in the reflection wavefront 212 (e.g., is the reflection wavefront 212 flat or curved). The aberrations detected by the wavefront sensor 214 can arise from multiple sources. For example, the aberrations detected by the reflection wavefront 212 can be associated with the eye of the observer 202, including spherical refractive errors, cylindrical refractive errors, astigmatism, other low order aberrations, and/or high order aberrations. The aberrations can also result from dynamic sources, such as tear film in the eye of the observer 202 that naturally arises during the surgical procedure. Further, the aberrations can be associated with the structure of optical elements of the microscope 206, such as one or more lenses 222. The wavefront sensor 214 can be any suitable device for detecting optical aberrations, including a Shack-Hartmann wavefront sensor, a Talbot-Moire wavefront sensor, a Tscherning aberrometer, a laser ray tracing aberrometer, or other aberrometry device(s). The wavefront sensor 214 can be in communication with the computing device 238. For example, the deformations in the reflection wavefront 212 detected by the wavefront sensor 214 can be received at the computing device 238.

Referring again to FIG. 1, in some embodiments, the method 100 can include determining aberrations in the reflection wavefront 212 resulting from the optical elements in the optical path between the observer and the subject. For example, as shown in FIGS. 2 and 3, the lenses 222 can be disposed in the optical path 240 between the observer 202 and the subject 204. The lenses 222 can be part of the eyepiece 236 and/or the body of the microscope 206. The microscope 206 can include an optics correction device 216 for determining and compensating for optical aberrations associated with the structure of the lenses 222. For example, the optics correction device 216 can identify and compensate for optical aberrations from the optical elements. In embodiments of the microscope 206 that include the optics correction device 216, the aberrations determined by the wavefront sensor 214 can include those arising from vision problems and/or dynamic errors of the observer 202 because the optics correction device 216 mathematically compensates for the aberrations arising from the optical elements of the microscope 206. Microscope optics errors can be identified during production (e.g., calibration) of the microscope 206. For example, in some embodiments, the reflection wavefront from an ideal source (e.g., known not have any optical aberrations) can be detected and stored. Any aberrations in the ideal reflection wavefront can be the result of microscope optics errors. The ideal reflection wavefront can be compared to the reflection wavefront 212 from the observer 202. Recall that the reflection wavefront 212 can include aberrations from the observer 202 and the optical elements. The difference between the ideal reflection wavefront and the reflection wavefront 212 can be associated solely with optical aberrations of the observer 202 and not the optical elements of the microscope 206.

Referring again to FIG. 1, the method 100 can include, at step 130, projecting a second light beam at the eye of a subject. The method 100 further includes, at step 140, determining aberrations in a second reflection wavefront associated with the second light beam. Steps 130 and 140 can be associated with identifying optical aberrations of the subject. Steps 130 and 140 can be similar to steps 110 and 120 described above.

As shown in FIGS. 2 and 3, the microscope 206 can include similar components in the optical path associated with the subject 204 as those in the optical path associated with the observer 202 described above. For example, the microscope 206 can include a light source 224. At step 130 (FIG. 1), the light source 224 can be configured to project a second light beam at an eye of the subject 204. The light source 224 can be configured to continuously or intermittently project the second light beam at the eye of the subject 204. The light source 224 can be in communication with the computing device 238. The computing device 238 can be configured to generate a control signal for and provide the control signal to the light source 224. The control signal can be based on a second wavefront compensation frequency. For example, second light beam can be projected at a relatively higher frequency, such that wavefront compensation is performed continuously or quasi-continuously. For example, the second light beam can be projected once approximately every 0.5 seconds, every 1 second, every 2 seconds, every 5 seconds, every 10 seconds, every 30 seconds, every 1 minute, every 2 minutes, and other periods greater than, less than, and/or between those listed, to compensate both for static vision problems and for dynamic errors arising during the surgical procedure (e.g., saline solution in the eye of the subject 204). A reflection of the second light beam off of the eye of the subject 204 includes a reflection wavefront 226. The reflection wavefront 226 can be received at a wavefront sensor 228. The wavefront sensor 228 can be disposed in the optical path 242 of the reflection wavefront 226. At step 140 (FIG. 1), the wavefront sensor 228 can determine phase aberrations in the reflection wavefront 226 (e.g., is the reflection wavefront 226 flat or curved). The wavefront sensor 228 can be in communication with the computing device 238. Referring again to FIG. 1, in some embodiments, the method 100 can include determining aberrations in the second reflection wavefront resulting from the optical elements in the optical path between the observer and the subject. For example, as shown in FIGS. 2 and 3, the microscope 206 can include an optics correction device 230 for determining and compensating for optical aberrations associated with the structure of the lenses 222.

Referring again to FIG. 1, the method 100 can include, at step 150, controlling an adaptive optical element disposed in the optical path between the observer and the subject to modify a phase of light in the optical path to compensate for the aberrations in the first and second reflection wavefronts. The adaptive optical element can be in communication with the computing device 238 (FIGS. 2 and 3). The computing device 238 can include any suitable processor or processing circuit for generating a control signal for the adaptive optical element to compensate for wavefront deformations in the reflection wavefronts 212 and/or 226. The control signal for the adaptive optical element can be generated based on the wavefront deformations detected by the wavefront sensors 214 and/or 228, and received at the computing device 238. The computing device 238 can provide the control signal to the adaptive optical element. As a result, the adaptive optical element compensates for optical aberrations by modifying the phase of incident light (e.g., modifying a curved wavefront such that it becomes flat). The adaptive optical element is configured to compensate for optical aberrations resulting from spherical refractive errors, cylindrical refractive errors, astigmatism, other low order aberrations, high order aberrations, dynamic errors, and/or microscope optics errors.

Referring now to FIG. 2, the adaptive optical element can include a reflective element 218 and/or a reflective element 232. For example, the reflective elements 218 and 232 can include deformable mirrors or other suitable reflective component(s). The reflective elements 218 and 232 can be disposed in the optical path 240 between the observer 202 and the subject 204. The reflective element 218 can be configured to compensate for wavefront deformations associated with the observer 202, and the reflective element 232 can be configured to compensate for wavefront deformations associated with the subject 204. The reflective elements 218 and 232 can be deformable in response to the control signal from the computing device 238 to modify the phase of incident light to compensate for the aberrations in the reflection wavefronts 212 and 226.

Referring now to FIG. 3, the adaptive optical element can include a transmissive element 234. For example, the transmissive element 234 can include a translucent (liquid crystal display or LCD) microdisplay, liquid lens, or other suitable transmissive component(s). For example, the transmissive element 234 can include a spatial light modulator available from HOLOEYE Photonics AG of Berlin-Adlershof, Germany. The transmissive element 234 can be disposed in the optical path 240 between the observer 202 and the subject 204. In some embodiments, the microscope 206 includes one transmissive element 234 to compensate for wavefront deformations associated with both the observer 202 and the subject 204. In some embodiments, the microscope 206 includes two or more transmissive elements 234. A parameter of the transmissive element 234 can be adjustable in response to the control/electrical signal from the computing device 238 to modify the phase of incident light to compensate for the aberrations in the reflection wavefronts 212 and 226. The parameter of the transmissive element can be adjustable, in response to the control/electrical signal, to modify the phase of incident light with a given spatial resolution. Thus, in some embodiments, controlling the adaptive optical/transmissive element in the method 100 can include providing the control/electrical signal to modify the phase of incident light with a given spatial resolution. For example, the parameter can be an electric field associated with the transmissive element 234. In an embodiment in which the transmissive element 234 includes an LCD, providing an electrical signal to modify the electric field can cause the orientation of the liquid crystals to shift, resulting in a change in the refractive index of the LCD. Because of the change in the refractive index, the phase of incident light can be modulated as the light passes through the LCD.

In some embodiments, the method 100 including compensating for wavefront deformations associated with both the eye of the observer 202 and the eye of the subject 204. In such embodiments, the microscope 206 includes wavefront compensation components for both the observer 202 and the subject 204 (e.g., the light sources 208 and 224, the wavefront sensors 214 and 228, the reflective elements 218 and 232, etc.). In some embodiments, the method 100 can include selectively performing the projecting, determining, and controlling steps to compensate for aberrations in one of the reflection wavefronts 212 and 226. For example, the microscope 206 can include only wavefront compensation components for one of the observer 202 and the subject 204 (e.g., one of the light sources 208 and 224, one of the wavefront sensors 214 and 228, one of the reflective elements 218 and 232, etc.). For example, the projecting, determining, and controlling steps can be performed to compensate for aberrations in the reflection wavefronts 212 and 226 at different times or with different frequencies. For example, the microscope 206 can include wavefront compensation components for both the observer 202 and the subject 204, but each set of components can be electronically switched on and off (or otherwise activated and deactivated) at different times or with different frequencies. For example, the observer 202, such as a surgeon, can choose to compensate for his or her own wavefront errors (e.g., aberrations in the reflection wavefront 212) once a day or once per surgical procedure. At the same time, the surgeon can choose to compensate for the wavefront errors of the subject 204 (e.g., aberrations in the reflection wavefront 226) continuously or quasi-continuously during the surgical procedure (e.g., every 0.5 seconds, every 1 second, every 2 seconds, every 5 seconds, every 10 seconds, every 30 seconds, every 1 minute, every 2 minutes, etc.). The surgeon can also choose to perform wavefront compensation for his or her own wavefront errors in a continuous or quasi-continuous manner during the surgical procedure. In an embodiment of the microscope 206 includes reflective adaptive optics, the reflective elements 218 and 232 become flat when phase compensation in the respective optical path is electronically switched off or otherwise deactivated.

The microscope 106 can be a monocular or binocular microscope. Thus, while FIGS. 2 and 3 include one eyepiece 236, it is understood that the microscope 106 can include one eyepiece for each eye of one or more observers 202 (e.g., two eyepieces each for a surgeon and an assistant). The teaching of the present disclosure can be implemented such that wavefront compensation is performed for one or more eyepieces. The microscope 106 can be a compound or stereo microscope. The teaching of the present disclosure can be implemented in one or more optical paths of the microscope 106. For example, one set of the wavefront compensation components (e.g., the light sources 208 and 224, the wavefront sensors 214 and 228, the adaptive optical element, etc.) can be implemented in the single optical path between the observer 202 and the subject 204 in a compound microscope. For example, one set of wavefront compensation components can be implemented in each of the two optical paths between the observer 202 and the subject 204 in a stereo microscope. In some embodiments, wavefront compensation can be separately performed for each eye of the observer 202. In some embodiments, the separate wavefront compensation for each optical path is combined (e.g., by the computing device 238) before being provided to eyes of the observer 202. In some embodiments, wavefront compensation can be separately performed for each of multiple observers 202 (e.g., for one eye of each observer, separately for each eye of each observer, etc.).

The devices, systems, and methods described herein are not limited to surgical microscopes. Teachings of the present disclosure can be implemented in slit lamps and/or diagnostic devices such as fundus cameras. For example, fundus cameras include complex optics to compensate for optical aberrations. Implementing the teachings of the present disclosure in a fundus camera can reduce the complexity of fundus camera optics while compensating for optical aberrations.

Embodiments as described herein can provide devices, systems, and methods that provide an ophthalmic surgical microscope with adaptive optical element(s) and wavefront sensor(s) to compensate for wavefront deformations associated with spherical and/or cylindrical refractive errors, astigmatism, low order aberrations, high order aberrations, and/or dynamic errors. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic surgical microscope disposed in an optical path between an observer and a subject, comprising:
   a first light source configured to project a first light beam at an eye of the observer, a reflection of the first light beam from the eye of the observer including a first reflection wavefront;
   a first wavefront sensor disposed in an optical path of a reflection of the first light beam from the eye of the observer, the optical path of the reflection at least partially overlapping the optical path between the observer and the subject, the first wavefront sensor being configured to determine aberrations corresponding to the eye of the observer in a first reflection wavefront of the reflection of the first light beam;
   a second light source configured to project a second light beam at an eye of the subject;
   a second wavefront sensor disposed in an optical path of a reflection of the second light beam, the second wavefront sensor being configured to determine aberrations corresponding to the eye of the subject in a second reflection wavefront of the reflection of the second light beam, the second wavefront sensor distinct from the first wavefront sensor;
   an adaptive optical element disposed in the optical path between the observer and the subject, the adaptive optical element being configured to modify the phase of incident light to compensate for the aberrations in the first reflection wavefront and the second reflection wavefront in response to a plurality of control signals; and
   a computing device in communication with the first wavefront sensor and the adaptive optical element, the computing device being configured to:
      generate a first control signal to compensate for the aberrations in the first reflection wavefront;
      provide the first control signal to the adaptive optical element;
      generate a second control signal to compensate for the aberrations in the second reflection wavefront;
      provide the second control signal to the adaptive optical element.

2. The ophthalmic surgical microscope of claim 1, wherein:
   the first and second light sources are configured to intermittently project the first and second light beams in response to light source control signals received from the computing device; and
   the computing device is in communication with the first and second light sources, the computing device being configured to generate the light source control signals based on respective wavefront compensation frequencies and to provide the light source control signals to the first and second light sources.

3. The ophthalmic surgical microscope of claim 1, wherein the first and second light sources comprise at least one of a laser source and super-luminescent diode(s).

4. The ophthalmic surgical microscope of claim 1, wherein the first and second wavefront sensors comprise at least one of: a Shack-Hartmann wavefront sensor, a Talbot-Moire wavefront sensor, a Tscherning aberrometer, a laser ray tracing aberrometer, or other aberrometry device(s).

5. The ophthalmic surgical microscope of claim 1, further comprising:
a first optics correction device disposed in the optical path of the reflection of the first light beam from the eye of the observer, the first optics correction device being configured to compensate for aberrations of the first reflection wavefront resulting from optical elements in the optical path between the observer and the subject; and
a second optics correction device disposed in the optical path of the reflection of the second light beam from the eye of the observer, the second optics correction device being configured to compensate for aberrations of the second reflection wavefront resulting from the optical elements in the optical path between the observer and the subject.

6. The ophthalmic surgical microscope of claim 1, wherein the adaptive optical element includes first and second reflective elements, the first and second reflective elements being deformable in response to the control signals signal to modify a phase of light in the optical path between the observer and the subject to compensate for aberrations in the first and second reflection wavefronts.

7. The ophthalmic surgical microscope of claim 1, wherein the adaptive optical element includes a transmissive element, wherein a parameter of the transmissive element is adjustable in response to the first control signal to modify the phase of incident light to compensate for the aberrations in the first reflection wavefront.

8. The ophthalmic surgical microscope of claim 7, wherein the parameter of the transmissive element is adjustable, in response to an electrical signal, to modify the phase of incident light with a given spatial resolution.

9. The ophthalmic surgical microscope of claim 1, wherein the adaptive optical element is configured to modify the phase of incident light to compensate for at least one of: spherical refractive errors, cylindrical refractive errors, errors associated with astigmatism, low order aberrations, high order aberrations, and dynamic errors.

10. A method of compensating for optical aberrations in an ophthalmic surgical microscope disposed in an optical path between an observer and a subject, comprising:
projecting a first light beam at an eye of an observer;
determining, by a first wavefront sensor, aberrations corresponding to the eye of the observer in a first reflection wavefront of a reflection of the first light beam from the eye of the observer, an optical path of the reflection at least partially overlapping the optical path between the observer and the subject;
projecting a second light beam at an eye of the subject;
determining, by a second wavefront sensor, aberrations corresponding to the eye of the subject in a second reflection wavefront of a reflection of the second light beam from the eye of the subject, the second wavefront sensor distinct from the first wavefront sensor; and
controlling an adaptive optical element disposed in the optical path between the observer and the subject to modify a phase of light in the optical path to compensate for the aberrations in the first and second reflection wavefronts by:
generating a first control signal to compensate for the aberrations in the first reflection wavefront;
providing the first control signal to the optical element;
generating a second control signal to compensate for the aberrations in the second reflection wavefront; and
providing the second control signal to the adaptive optical element.

11. The method of claim 10, further comprising:
controlling the first light source to intermittently project the first light beam based on a first wavefront compensation frequency; and
controlling the second light source to intermittently project the second light beam based on a second wavefront compensation frequency.

12. The method of claim 10, wherein determining aberrations in the first and second reflection wavefronts includes:
receiving the first and second reflection wavefronts respectively at the first and second wavefront sensors comprising at least one of a Shack-Hartmann wavefront sensor, a Talbot-Moire wavefront sensor, a Tscherning aberrometer, a laser ray tracing aberrometer, or other aberrrometry device(s).

13. The method of claim 10, further comprising:
determining aberrations in the first and second reflection wavefronts resulting from optical elements in the optical path between the observer and the subject.

14. The method of claim 10, wherein controlling the adaptive optical element includes controlling first and second reflective elements disposed in the optical path between the observer and the subject, the first and second reflective elements being deformable to modify a phase of light in the optical path between the observer and the subject to compensate for aberrations in the first and second reflection wavefronts.

15. The method of claim 10, wherein controlling the adaptive optical element includes controlling a transmissive element disposed in the optical path between the observer and the subject, a characteristic of the transmissive element being adjustable to modify a phase of light in the optical path between the observer and the subject to compensate for aberrations in the first and second reflection wavefronts.

16. The method of claim 15, wherein controlling the transmissive element includes providing an electrical signal to the transmissive element to modify the phase of incident light with a given spatial resolution.

17. The method of claim 10, wherein the aberrations in the first and second reflection wavefronts include at least one of: spherical refractive errors, cylindrical refractive errors, errors associated with astigmatism, low order aberrations, high order aberrations, and dynamic errors.

18. The method of claim 10, further comprising:
selectively performing the projecting, determining, and controlling steps to compensate for aberrations in one of the first and second reflection wavefronts.

* * * * *